(12) United States Patent
Muszak et al.

(10) Patent No.: US 7,329,046 B1
(45) Date of Patent: Feb. 12, 2008

(54) DIGITAL RADIOGRAPHY IMAGING SYSTEM WITH ROTATABLE DISPLAY AND CONTROLS

(75) Inventors: Jerald J. Muszak, Henrietta, NY (US); Michael Venturino, Geneseo, NY (US); Nancy E. Laurie, Hilton, NY (US); John M. Staton, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 11/522,868

(22) Filed: Sep. 18, 2006

(51) Int. Cl.
H05G 1/02 (2006.01)

(52) U.S. Cl. .................. 378/197; 378/196

(58) Field of Classification Search ....... 378/196–198, 378/193, 189
See application file for complete search history.

(56) References Cited

U.S. PATENT DOCUMENTS 3,702,935 A 11/1972 Carey et al.
4,674,107 A 6/1987 Urban et al.
6,609,826 B1* 8/2003 Fujii et al. .................. 378/198

FOREIGN PATENT DOCUMENTS

WO 2004/064639 8/2004

* cited by examiner

Primary Examiner—Hoon Song

(57) ABSTRACT

A digital radiography system for imaging a subject. A support structure, coupled to an X-ray source and an X-ray imaging detector, is rotatable about a first axis and is linearly moveable. The X-ray source and the X-ray imaging detector are also rotatable about second and third axes, respectively, to provide an operator with a number of degrees of freedom to move the X-ray source and the X-ray imaging detector to different positions relative to a subject. Further, the system has means for coupling an operator control interface and a display to the X-ray source for permitting an operator to rotate them about a fourth axis so that the operator control interface and display are accessible to the operator such that the position of the operator does not have to change when the positions of the X-ray source and the X-ray detector are changed.

9 Claims, 8 Drawing Sheets

DIGITAL RADIOGRAPHY IMAGING SYSTEM WITH ROTATABLE DISPLAY AND CONTROLS

FIELD OF THE INVENTION

The invention relates generally to digital radiography imaging systems having an X-ray source and an X-ray imaging detector that are moveable among various positions to accommodate a variety of physical characteristics of a subject, and more particularly to an operator control interface for such an imaging system.

BACKGROUND OF THE INVENTION

Some digital radiography imaging systems have an X-ray source and an X-ray imaging detector that are coupled together and supported in a manner that provides for a plurality of degrees of freedom of movement so that the imaging system can be properly positioned relative to a subject. Often, an operator control interface having a display screen is integrated into the system. A problem occurs when an operator needs to access the control interface and it has been shifted out of a convenient position for maintaining control of the apparatus by the movement of the imaging system.

There are prior systems that are adapted to maintain a correct viewing orientation of the image on the operator control interface with respect to the operator by adjusting the image on the display screen to compensate for the tilting movement of the X-ray source and an X-ray imaging detector. That is, the image to be displayed is modified in accordance with the tilting movement. The image data stored in memory is remapped from memory locations to positions on the display screen in order to display the image on the screen in a desired orientation. Such systems require re-computation, resizing, and redrawing of the image on the display screen in conjunction with the movement of the patient table. The readability and legibility of the display suffer due to angularities of the screen text in relationship to the operator. See, for example, U.S. Pat. No. 4,674,107 wherein orientation of an image on a display is maintained constant with respect to a main support during pivotal motion of the X-ray system by rotating the displayed image as a function of the direction and extent of the pivotal motion. PCT Application WO 2004/064039 discloses an imaging device with means for rendering the detector orientation and the display orientation essentially equal, but does not disclose maintaining a particular orientation of the display relative to an observer.

Other digital radiography imaging systems will "flip" and redraw the image on the display screen after the display and X-ray source have been subject to a given amount of angular rotation (e.g., a 45 degree angle in either direction) by an operator in positioning the source.

In other digital radiography imaging systems such as shown in U.S. Pat. No. 3,702,035, the display screen is mounted on an independent support arm that does not move in conjunction with the movement of X-ray source. Rather, it maintains a fixed position. Such systems have limited ability to handle different orientations of individuals for imaging, and must include additional support structure for the display monitor. Furthermore, such systems occupy significant floor space, which is disadvantageous in emergency room situations.

There exists a need for a digital radiography system that has a display and controls that are always in the same orientation for an operator. Additionally, there exists a need for ergonomic features for controlling the operation of an imaging system with an X-ray source and detector in a variety of positions.

SUMMARY OF THE INVENTION

The present invention provides a digital radiography system with an operator control interface and display that can be moved with degrees of freedom so as to maintain the same orientation with respect to an operator when the X-ray source and X-ray imaging detector are positioned to capture an image of a subject.

The present invention is intended for use in radiography systems having an X-ray source, an X-ray imaging detector, and a support structure coupling the X-ray source and the X-ray detector, wherein the support structure is rotatable about a predetermined axis such as to position the X-ray source and the X-ray imaging detector at various rotational positions about a subject. In accordance with a feature of the invention, an operator control interface is mounted on the radiography system for rotation about an axis that is substantially parallel to the predetermined axis such that relative orientation between the operator control interface and the operator can remain constant when the support structure rotates about said predetermined axis.

In a preferred embodiment of the invention, the predetermined axis is substantially horizontal when the radiography system is in use. The operator control interface includes a first display having a scene orientation with a top and a bottom, the scene orientation remaining constant when the support structure rotates about said predetermined axis. A second display having a scene orientation with a top and a bottom may be provided such that the scene orientation of the second display remains constant when the support structure rotates about the predetermined axis.

One advantage of the present invention is that it is a compact, adjustable digital radiography imaging system where the X-ray source and X-ray imaging detector are capable of being positioned in at least the same positions achievable with conventional floor mounted systems, with the additional feature of providing a display and controls which have a given orientation with respect to the operator. Typical imaging systems are generally much larger, or have separate pieces of equipment that work together. These systems are more mechanically complex, and have disadvantages in usability, cost and reliability. The adjustability of the present invention allows an operator to position the X-ray source and X-ray imaging detector to achieve suitable positioning to accommodate subjects for imaging (including ambulatory and non-ambulatory patients standing, reclining or in seated position), and provides a display and controls which retain the same orientation with respect to the operator. Thus, the operator control interface and display of the present invention is accessible to the operator so that the position of the operator does not have to change when the position of the X-ray source and X-ray imaging detector are changed. The position of the operating control interface and its display relative to the operator is important for critical environments, such as emergency or trauma rooms. The advantages of the operator control interface include, but are not limited to, greater legibility and readability of the display, less errors made by an operator in orienting the system to procure images, and other related advantages. By virtue of its size and placement of the operator control interface relative to the operator, this invention minimizes the potential for injury to an operator or patient by accidental contact with the hardware. Moreover, this invention can minimize the potential for collision between with obstructions in the installation environment by providing the operator with familiar controls.

BRIEF DESCRIPTION OF THE DRAWINGS

The foregoing and other objects, features, and advantages of the invention will be apparent from the following more particular description of the embodiments of the invention, as illustrated in the accompanying drawings.

DETAILED DESCRIPTION OF THE INVENTION

Figure 1:
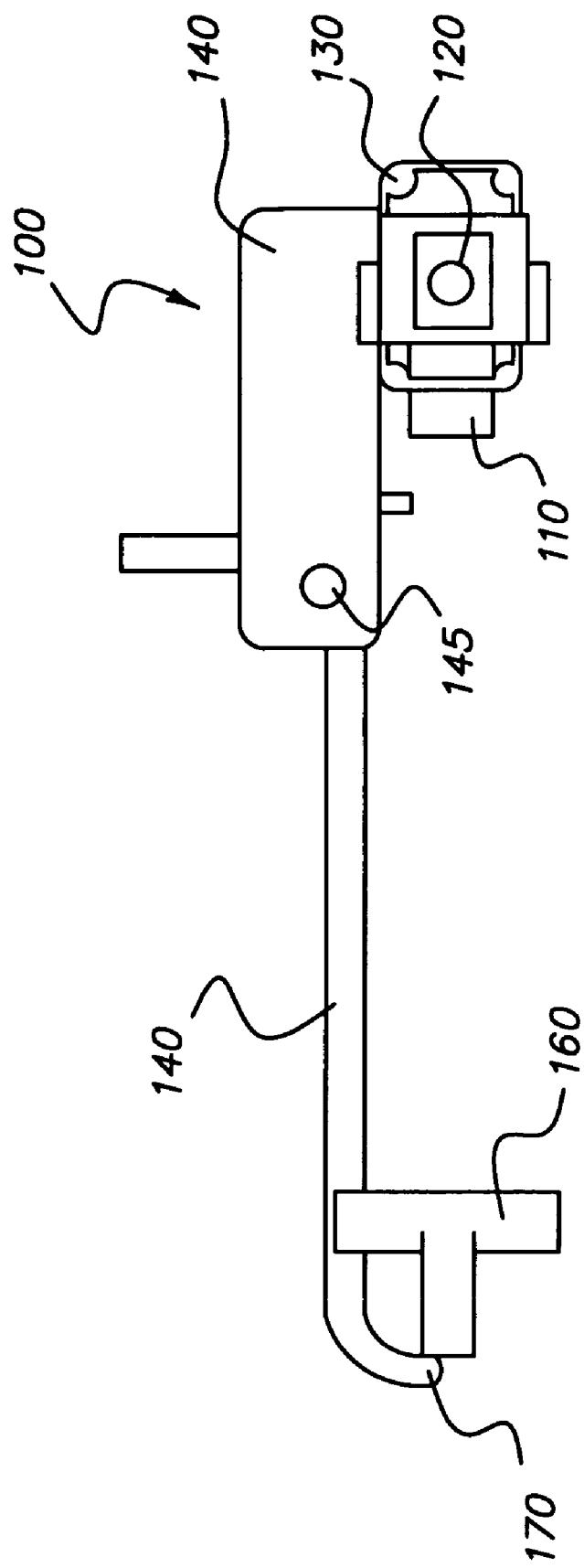
FIG. 1 shows a digital radiography system in accordance with the present invention.

The following is a detailed description of the preferred embodiments of the invention, reference being made to the drawings in which the same reference numerals identify the same elements of structure in each of the several figures.

Figure 4:
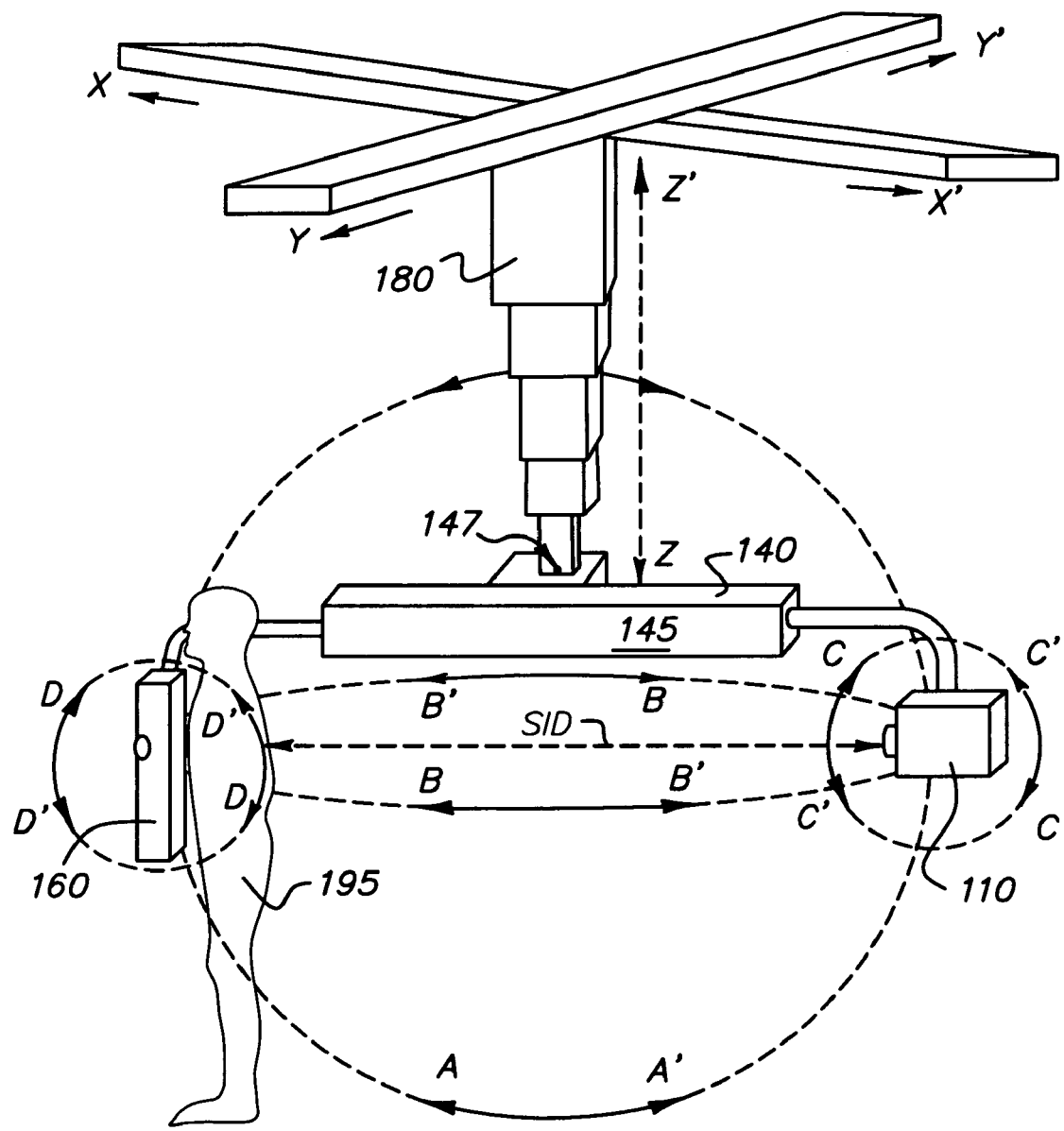
FIG. 4 shows a diagrammatic view of the digital radiography system of FIG. 1 and it's labeled X, Y, Z, A, B, C and D axes with a subject to be imaged in a standing position.
Figure 5:
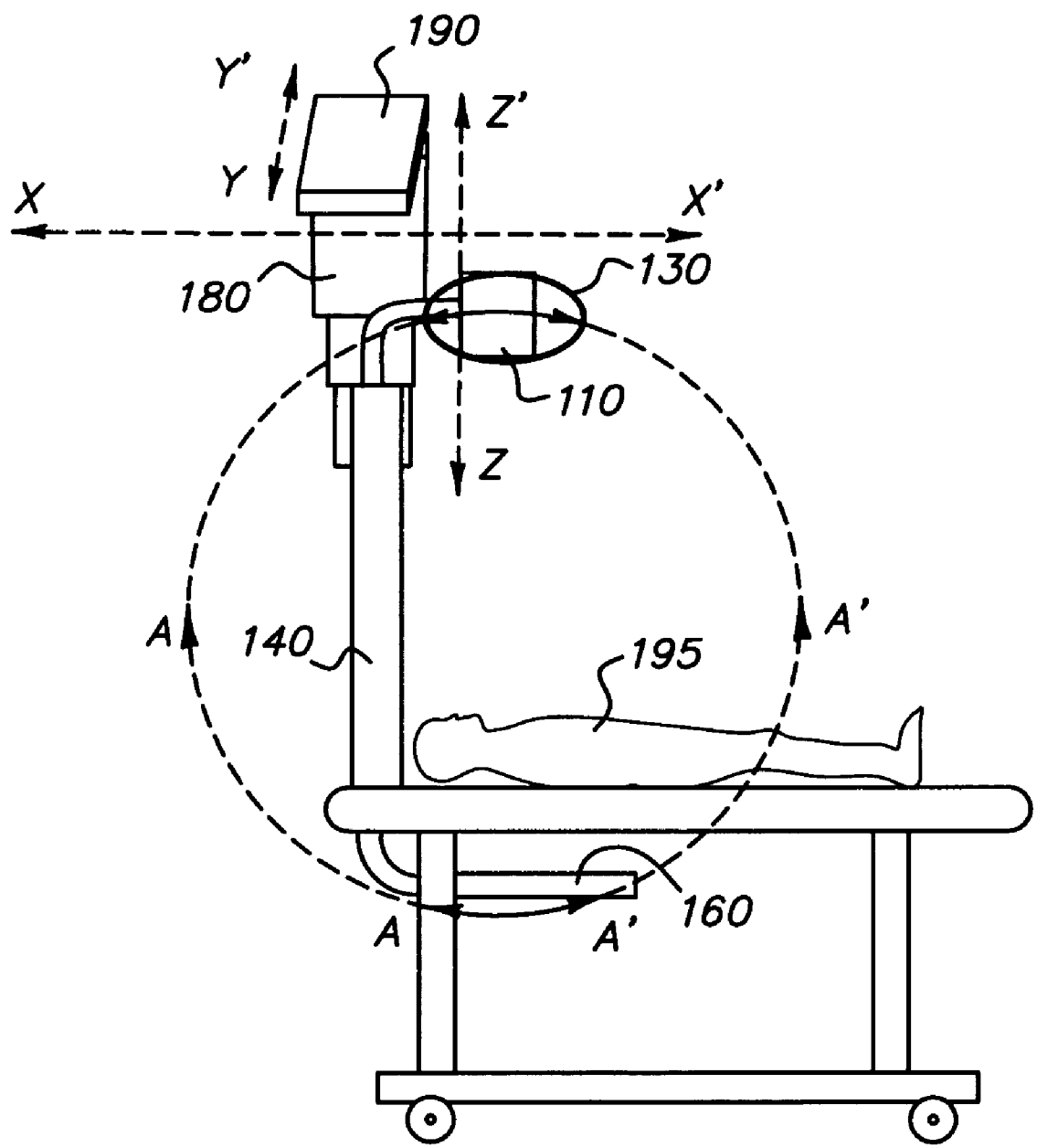
FIG. 5 shows a diagrammatic view of the digital radiography system of FIG. 1 with a subject to be imaged in a reclined position.
Figure 6:
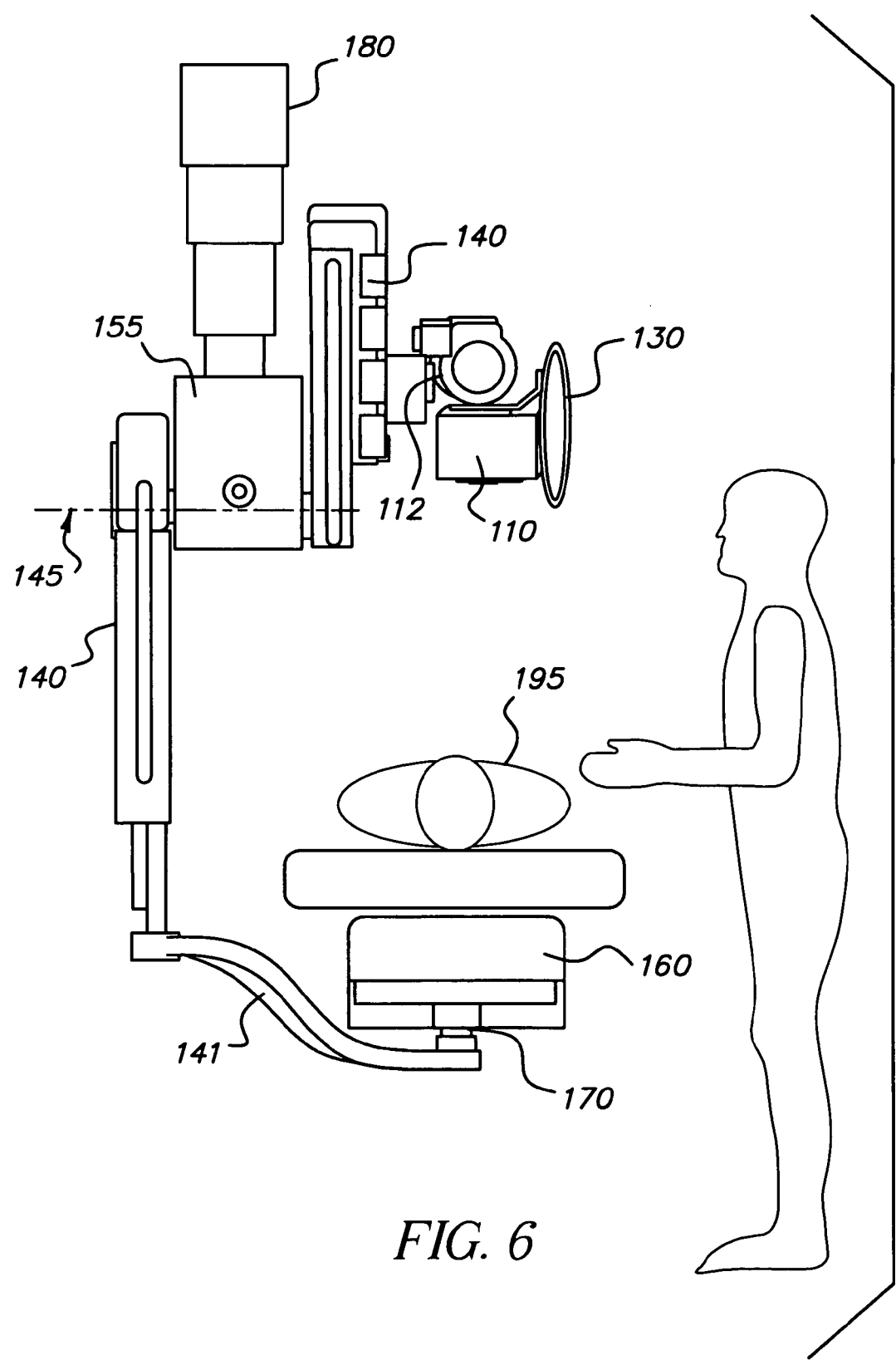
FIG. 6 shows another diagrammatic view of the digital radiography system of FIG. 1 with a subject to be imaged in a reclined position.
Figure 7:
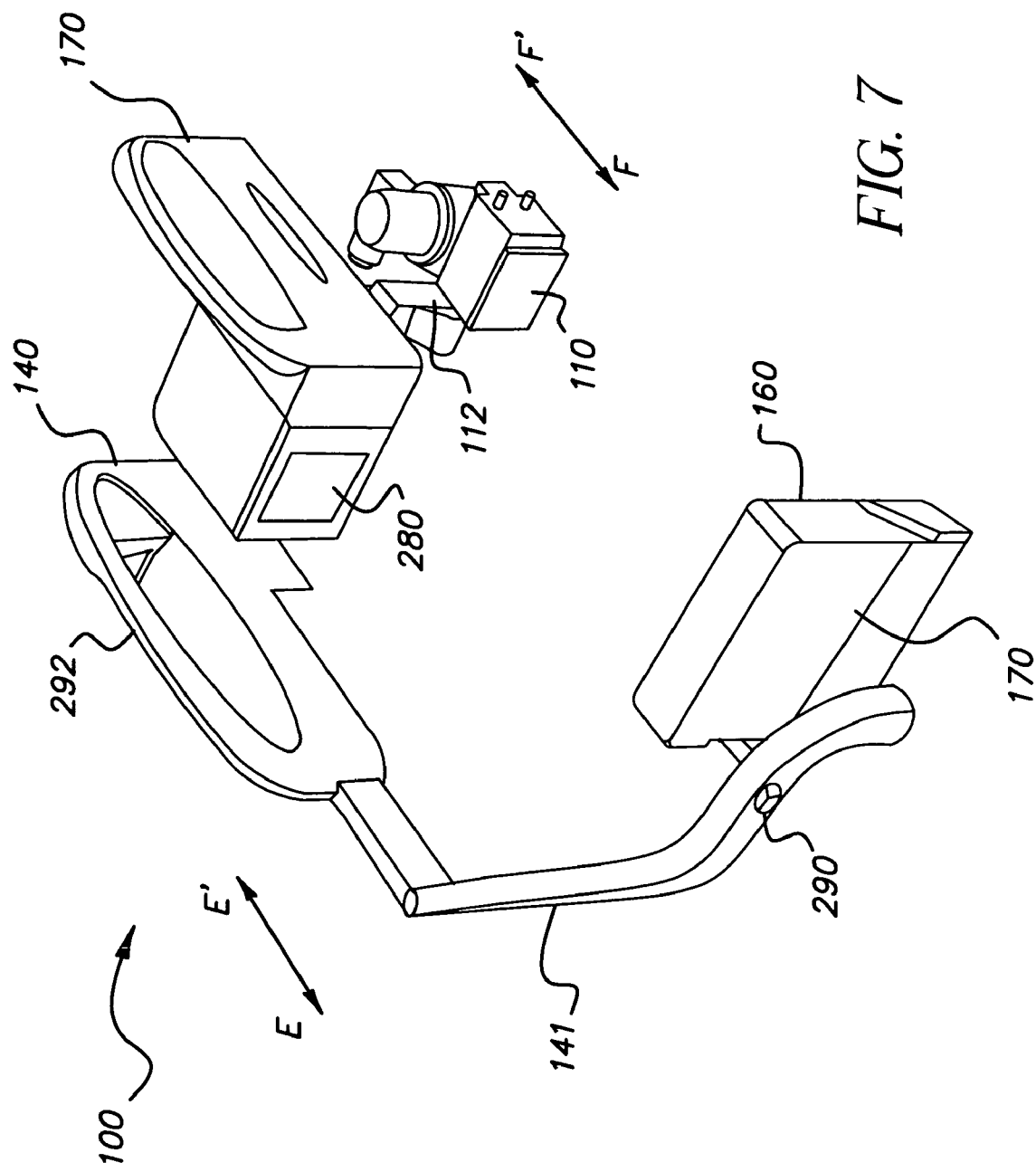
FIG. 7 shows another diagrammatic view of the support structure, X-ray source and X-ray imaging detector of the digital radiography system of FIG. 1.

Referring to FIG. 1, a digital radiography system 100 has an X-ray source 110, a first display 120, an operator control interface 130, a support structure 140, and an X-ray imaging detector 160 with a coupling 170. X-ray source 110 is connected to a support structure 140 by a coupling 112 (see FIGS. 6-7) that allows X-ray source 110 to rotate in the C and C' directions (shown in FIG. 4). Coupling 170 permits X-ray imaging detector 160 to move in the D and D' directions (illustrated in FIG. 4), and to rotate so as to orient X-ray imaging detector 160 into a portrait or landscape position. Support structure 140 is pivotally mounted for rotation about an axis 145 as illustrated in FIG. 4. Support structure 140 is linearly adjustable (e.g., in the E and E' directions shown in FIG. 7) so as to allow an operator to set the source-to-image distance between X-ray source 110 and X-ray imaging detector 160. X-ray source 110 is linearly moveable in directions F and F' (shown in FIG. 7) along support structure 140 so as to adjust the source-to-image distance before capturing an image of a subject as shown in FIGS. 4-6. Support structure 140 is further rotatable about axis an 145 in the A and A' directions illustrated in FIG. 4 by an operator in preparation for capturing an image of subject 195.

Figure 3B:
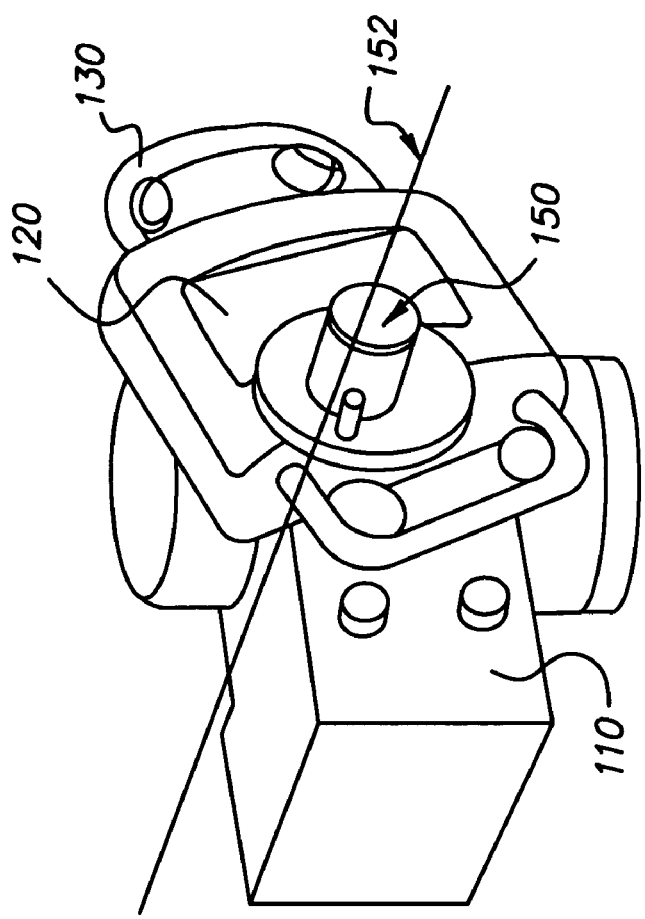
FIGS. 3A and 3B show the coupling between the X-ray source and operator controls of the digital radiography system of FIG. 1.
Figure 3A:
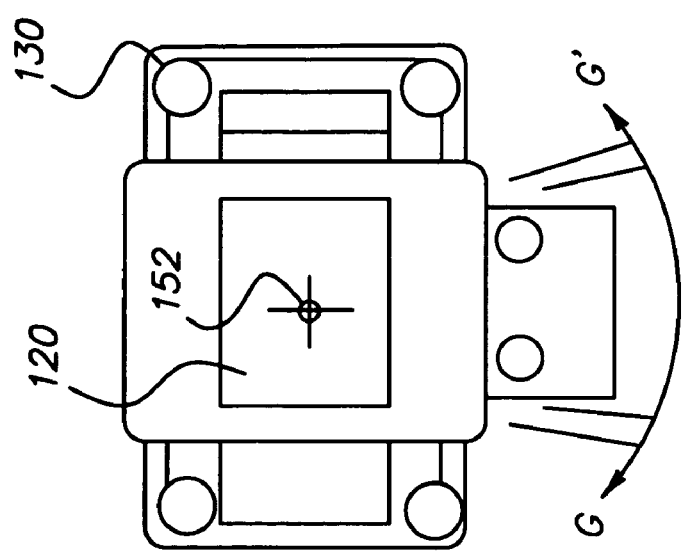

Operator control interface 130 and first display 120 are mounted for movement about an axis 152 in the G and G' directions (see FIGS. 3A and 3B). Axis 152 is substantially parallel to axis 145. As used herein, the phrase "substantially parallel" is intended to mean that axis 145 and axis 152 are close enough to parallel so as to maintain the information presented on first display 120 close enough to the same orientation relative to an operator so that the position of the operator does not have to change when the positions of the X-ray source and the X-ray imaging detector are changed, regardless of the direction and extent that support structure 140 is rotated. Operator control interface 130 has grip points incorporated into its handle to maximize grasp by an operator. These grip points can be optimized to allow for left-handed or right-handed use.

As illustrated in FIGS. 4-6, support structure 140 is connected to telescoping support member 180 by a coupling 155 (see FIG. 6). The telescoping support member is designed to be suspended from a ceiling of a room by a moveable base 190 (illustrated in FIG. 5). Moveable base 190 can be attached to a typical ceiling-mounted X-Y rail structure using a carriage system with a plurality of wheels or other suitable movement system. Thus, with such an X-Y rail structure, moveable base 190 is selectably moveable in the X, X', Y and Y' directions illustrated in FIGS. 4 and 5. Moveable base 190 or coupling 155 can include a rotational mechanism, which is used in rotating telescoping support member 180 or support structure 140 about an axis 147 in the B and B' directions illustrated in FIG. 4.

Telescoping support member 180 is adjustable in the Z and Z' directions shown in FIGS. 4 and 5 to varying positions between a collapsed position and an extended position. That is, telescoping support member 180 is configured to slide inward and outward in overlapping sections. In a collapsed position, telescoping support member 180 is moved in the Z' direction and disposed towards moveable base 190 close to the ceiling. In an extended position, telescoping support member 180 is moved in the Z direction and is disposed away from moveable base 190 close to the floor. Telescoping support member 180 can move in Z and Z' directions to discrete positions intermediate of the collapsed and extended positions. This motion allows for the imaging of objects of various heights and orientations between the collapsed and extended positions.

Support structure 140 allows digital radiography system 100 to image a variety of subjects (e.g., subject 195 illustrated in FIGS. 4-6), which can be an individual or a body part of the individual), whether the subject is standing (e.g., see subject 195 of FIG. 4), reclining on a table (e.g., see subject 195 of FIGS. 5 and 6), or sitting. Support structure 140 is configured to slide inward and outward in overlapping sections in directions E and E' (shown in FIG. 7), so as to move the location of X-ray imaging detector 160. X-ray source 110 is moveable linearly to discreet positions in the F and F' directions (illustrated in FIG. 7) along support structure 140 to provide further adjustment of digital radiography system 100 for imaging. The positioning of X-ray source 110 and X-ray imaging detector 160 by an operator can achieve an appropriate source-to-image distance for imaging of the subject to occur. As indicated in FIG. 4, the source-to-image distance is the linear distance between X-ray source 110 and X-ray imaging detector 160.

Figure 8:
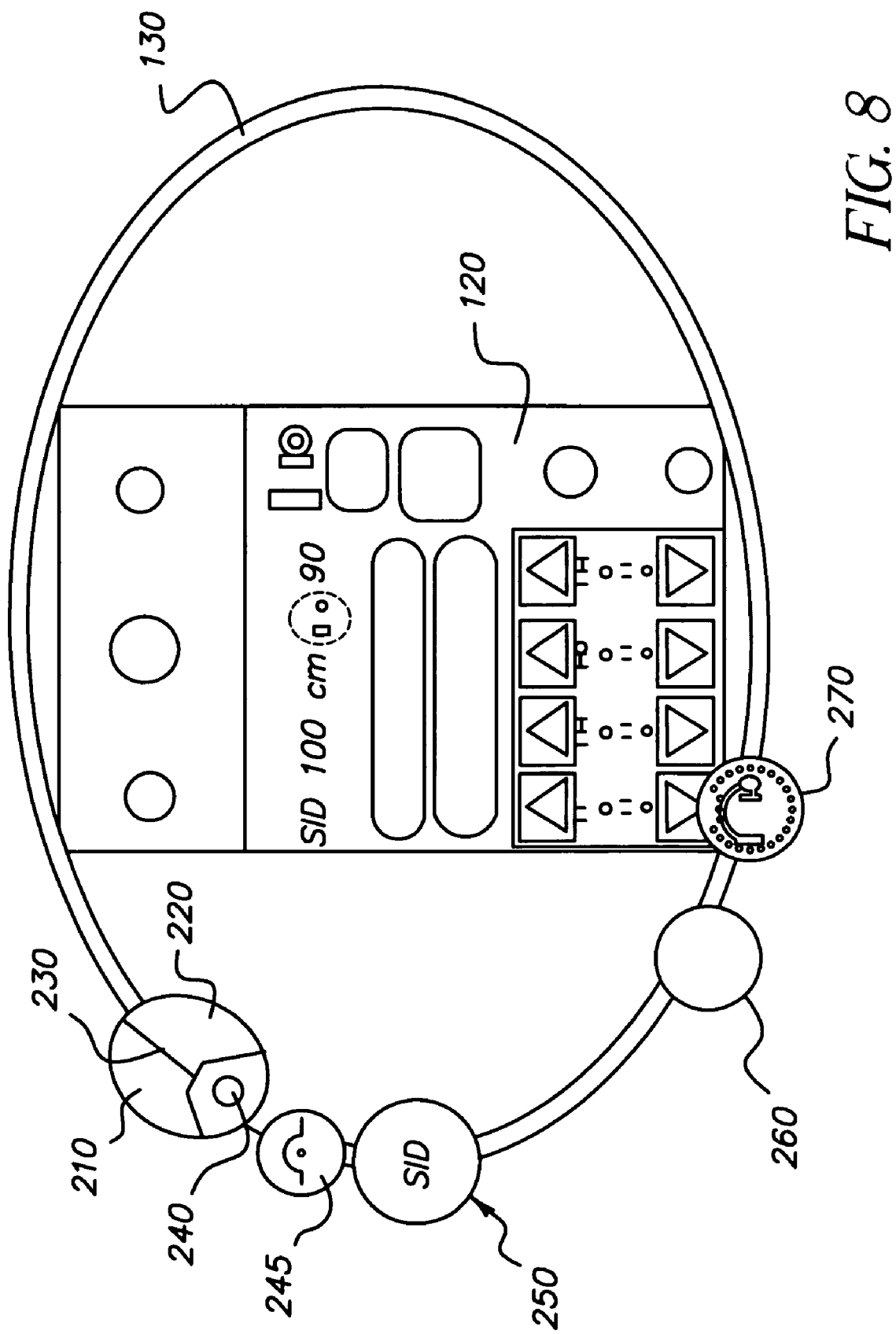
FIG. 8 shows a diagrammatic view of a display and operator control interface for a digital radiography system of FIG. 1.

FIG. 8 illustrates an exemplary display screen for first display 120 and control setup for operator control interface 130. As shown, operator control interface 130 has X-direction control 210, Y-direction control 220, Z-direction control 230, B-direction control 240, detent skip control 245, source-to-image distance release control 250, X-ray source tilt control 260, A-direction control 270, X-ray imaging detector release control (not shown), or any suitable combination thereof.

X-direction control 210 permits moveable base 190 to move in the X and X' directions (see FIG. 4). Similarly, Y-direction control 220 permits control the movement of moveable base 190 in the Y and Y' directions (see FIG. 4), and Z-direction control 230 permits adjustment of telescoping support member 180 in the Z and Z' directions. In other words, controls 210, 220, and 230 allow an operator to control the forward, back, left, right, up, or down movements of support structure 140. As described above, movement of base 190 in the X, X', Y, and Y' directions can be achieved through use of the rails on the ceiling, and movement in the Z and Z' directions is permitted by the sliding inward and outward of the overlapping sections of telescoping support member 180. B-direction control 240 allows an operator or technician to control the rotational motion of support structure 140 in a plane parallel to the ground (e.g., movement in the B and B' directions illustrated in FIG. 4 as illustrated in FIGS. 2 and 4).

Detent skip control 245 allows an operator to bypass detents (e.g., detents fixed by manufacturing or detents added through software configuration) that represent predefined amounts of movement of a structure about an axis or in a particular direction. Movement from detent to detent in a particular direction represents a predefined amount of movement in a direction or about an axis. The detents can be set by operators at particular locations that are expected to be common stoppage points of motion along an axis or direction. The detents permit the operator to reach these predefined points without overshooting, or the need of additional fine positioning adjustments. For example, detents can be used to define discrete amounts of movement for support structure 140 in the A, A', B, and B' directions illustrated in FIG. 4. Detents can also be used to define discrete amounts of movement of moveable base 190 in the X, X', Y, and Y' directions (see FIGS. 4 and 5). In another example, detents can be predefined for movement of X-ray source 110 in the C and C' directions, or detents can be predefined for X-ray imaging detector 160 in the D and D' directions. The detent will normally stop the motion of the structure at the detent point along a given direction or about an axis. By using detent skip control 245, the operator can move the device or structure without interruption.

Figure 2:
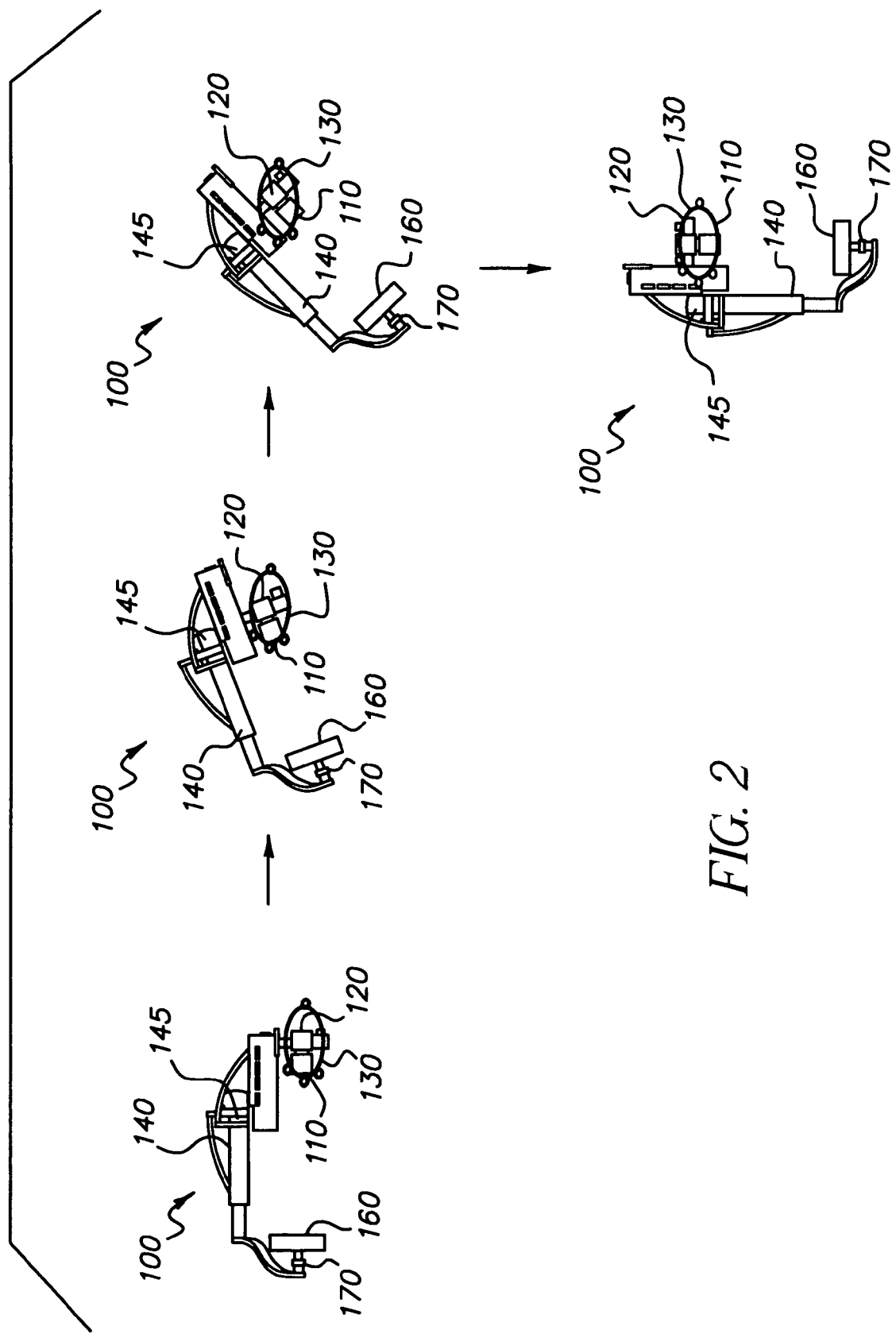
FIG. 2 is a series of views of the digital radiography system of FIG. 1 in various positions in accordance with present invention.

A-direction control 270 allows an operator or technician to rotate direct radiography system 100 in a plane perpendicular to the ground (e.g., movement about the A-axis as shown in FIG. 2). Source-to-image distance release control 250 can control movement of support structure 140 (for movement of X-ray imaging detector 160 in the E and E' directions indicated in FIG. 7). Using source-to-image distance release control 250, an operator can also move X-ray source 110 in the F and F' directions indicated in FIG. 7 on support structure 140 so as to change the source-to-image distance (as illustrated in FIG. 4) between X-ray source 110 and X-ray imaging detector 160. X-ray source tilt control 260 allows an operator or technician to adjust the angular movement of X-ray source 110 in the C and C' directions (as illustrated in FIG. 4).

Turning again to FIG. 7, digital radiography system 100 includes a second display 280 and second controls 290. Second display 280 is coupled to support structure 140 to provide an alternative display to an operator of the same information provided on first display 120. Second display 280 is fixed in a position on support structure 140 (in contrast to first display 120, where coupling 150 allows rotational movement of first display 120 and operator control interface 130 so as to maintain a consistent position relative to an operator). Second controls 290 or third controls 292 can provide duplicate controls for X-direction control 210, Y-direction control 220, Z-direction control 230, B-direction control 240, detent skip control 245, SID release control 250, X-ray source tilt control 260, A-direction control 270, D-direction control, or any suitable combination thereof (in addition to these controls being located on operator control interface 130 or on first display 120). These controls can have any suitable arrangement. These additional controls are advantageous, for example, if an operator or technician is located adjacent to second controls 290 or third controls 292, and he or she controls the operation and positioning of X-ray source 110 and X-ray imaging detector 160 of digital radiography system 100.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

100 Digital radiography system
110 X-ray source
112 Coupling
120 First Display
130 Operator control interface
140 Support structure
145 Axis
147 Axis
150 Coupling
152 Axis
170 Coupling
180 X-ray imaging detector
170 Coupling
180 Telescoping support member
190 Moveable base
195 Subject
210 X-direction control
220 Y-direction control
230 Z-direction control
240 B-direction control
245 Detent skip control
250 SID release control
260 X-ray source tilt control
270 A-direction control
280 Second display
290 Second controls
292 Third controls

The invention claimed is:

1. An apparatus comprising:
a radiography system including: an X-ray source, an X-ray imaging detector, and a rotatable support structure coupling the X-ray source and the X-ray detector, the support structure being rotatable about a first axis to position the X-ray source and the X-ray imaging detector at various rotational positions about a subject; and
an operator control interface mounted on the rotatable support structure for rotation about a second axis that is substantially parallel to the first axis such that the operator control interface can rotate around the substantially parallel axis so that the orientation between the operator control interface and the operator remains constant when the support structure rotates about the predetermined axis.

2. The apparatus as set forth in claim 1, wherein the first axis substantially horizontal when the radiography system is in use.

3. The apparatus as set forth in claim 1, wherein the operator control interface includes a first display having a scene orientation with a top and a bottom, the scene orientation remaining constant when the support structure rotates about the first axis.

4. The apparatus of claim 3, wherein the operator control interface includes a second display having a scene orientation with a top and a bottom, the scene orientation of the second display remaining constant when the support structure rotates about the first axis.

5. A digital radiography system with an operator control interface, comprising:
   an X-ray source;
   an X-ray imaging detector;
   a support structure coupled to the X-ray source and the X-ray detector and rotatable about a first axis and linearly moveable, the X-ray source and the X-ray imaging detector being rotatable relative to the support structure about second and third axes, respectively, to thereby provide an operator with a number of degrees of freedom of motion of the X-ray source and the X-ray imaging detector to move them to different positions relative to a subject; and
   an operator control interface attached to the support structure whereby the operator can position the X-ray source relative to the X-ray imaging detector, the operator control being coupled to the X-ray source such that the operator can to rotate the operator control interface about a fourth axis.

6. The digital radiography system of claim 5, adapted for linear movement of the X-ray source and the X-ray imaging detector relative to each other to change the distance between the X-ray source and the X-ray imaging detector.

7. The digital radiographic system of claim 5, wherein the operator control interface includes a first display.

8. The digital radiographic system of claim 5, further comprising a second display is affixed to the support structure.

9. The digital radiography system of claim 5, further comprising:
   a telescoping support member coupled to the support structure;
   a moveable base coupled to the telescoping support member opposite the support structure, wherein the moveable base is moveable along a predetermined path; and
   a coupler connected to the support structure and the telescoping support member that permits rotation of the support structure about a fifth axis.

* * * * *